(12) United States Patent
Miki et al.

(10) Patent No.: US 12,714,791 B2
(45) Date of Patent: Aug. 25, 2026

(54) INJECTOR

(71) Applicant: DAICEL CORPORATION, Osaka (JP)

(72) Inventors: Katsuya Miki, Tokyo (JP); Shingo Atobe, Tokyo (JP); Hiroshi Miyazaki, Tokyo (JP); Ayano Suzuki, Tokyo (JP); Yuko Sakaguchi, Tokyo (JP)

(73) Assignee: Daicel Corporation, Osaka (JP)

( * ) Notice: Subject to any disclaimer, the term of this patent is extended or adjusted under 35 U.S.C. 154(b) by 1036 days.

(21) Appl. No.: 16/968,095

(22) PCT Filed: Feb. 8, 2019

(86) PCT No.: PCT/JP2019/004722
§ 371 (c)(1),
(2) Date: Aug. 6, 2020

(87) PCT Pub. No.: WO2019/156237
PCT Pub. Date: Aug. 15, 2019

(65) Prior Publication Data

US 2021/0023302 A1 Jan. 28, 2021

(30) Foreign Application Priority Data

Feb. 9, 2018 (JP) ................................ 2018-021911

(51) Int. Cl.
*A61M 5/20* (2006.01)

(52) U.S. Cl.
CPC ................................ *A61M 5/2046* (2013.01)

(58) Field of Classification Search
CPC ....... A61M 5/2046; A61M 5/30; A61M 5/482
See application file for complete search history.

(56) References Cited

U.S. PATENT DOCUMENTS

2003/0176839 A1 9/2003 Chiwanga et al.
2005/0010168 A1 1/2005 Kendall
(Continued)

FOREIGN PATENT DOCUMENTS

JP 2002-511396 A 4/2002
JP 2004-358234 A 12/2004
(Continued)

OTHER PUBLICATIONS

International Search Report and Written Opinion mailed Mar. 26, 2019 in International Application No. PCT/JP2019/004722, in 17 pages.

(Continued)

*Primary Examiner* — William R Carpenter
(74) *Attorney, Agent, or Firm* — Knobbe, Martens, Olson & Bear, LLP

(57) ABSTRACT

This application relates to an injector that can directly inject a solution containing biomolecules into a cell nucleus of a wide range of injection targets with high efficiency. In one aspect, the injector injects a solution containing biomolecules into an injection target from an injector main body without performing injection through a given structure in a state where the given structure is inserted into the injection target. The injector may include an accommodation unit and a nozzle unit, wherein the injector satisfies given conditions.

5 Claims, 4 Drawing Sheets

(56) References Cited

U.S. PATENT DOCUMENTS

| | | | | |
|---|---|---|---|---|
| 2007/0043320 | A1* | 2/2007 | Kenany | A61M 37/00 604/68 |
| 2007/0079777 | A1* | 4/2007 | Hurlstone | F02B 71/00 123/46 R |
| 2013/0237951 | A1 | 9/2013 | Oda et al. | |
| 2015/0265770 | A1 | 9/2015 | Yoh | |
| 2018/0036485 | A1 | 2/2018 | Oda et al. | |
| 2018/0056003 | A1 | 3/2018 | Oda et al. | |
| 2018/0168789 | A1* | 6/2018 | Shiku | A61D 1/025 |
| 2018/0304019 | A1 | 10/2018 | Oda et al. | |
| 2019/0151552 | A1 | 5/2019 | Oda et al. | |
| 2021/0023302 | A1 | 1/2021 | Miki et al. | |

FOREIGN PATENT DOCUMENTS

| | | | | |
|---|---|---|---|---|
| JP | 2006-524079 | A | 10/2006 | |
| JP | 2006-325700 | A | 12/2006 | |
| JP | 2012-061269 | A | 3/2012 | |
| JP | 2017-000667 | A | 1/2017 | |
| JP | 7280201 | B2 | 5/2023 | |
| WO | WO 99/52463 | | 10/1999 | |
| WO | WO-2016187407 | A1 * | 11/2016 | A61K 39/0011 |
| WO | WO-2016204184 | A1 * | 12/2016 | A61D 1/025 |
| WO | WO 2017/115868 | A1 | 7/2017 | |

OTHER PUBLICATIONS

Extended Search Report dated Sep. 28, 2021 in European Application No. 19751322.9.

Miyazaki et al., "Development of Pyro-Drive Jet Injector With Controllable Jet Pressure", Journal of Pharmaceutical Sciences 108 (2019) 2415-2420.

* cited by examiner 8
9
7
71
6
10
5
2
4
1
3
32
31
31a

INJECTOR

The present application is a U.S. national phase application under 35 U.S.C. § 371 of International Application No. PCT/JP2019/004722, filed on Feb. 8, 2019, which claims the benefit of Japanese Patent Application No. 2018-021911 filed on Feb. 9, 2018, in the Japanese Patent Office, the entire disclosure of each of which is incorporated herein by reference.

TECHNICAL FIELD

The present invention relates to an injector. Specifically, the present invention relates to an injector, to a method of injecting a solution containing biomolecules into a cell nucleus of an injection target using the injector, and to a method of expressing a gene in an injection target.

BACKGROUND ART

Regarding injectors for injecting a drug solution into a living body or the like, there are catheters including an injection needle and a drive source for transporting a drug solution into an injection target in addition to a needle syringe that performs injection through an injection needle and a needleless syringe that performs injection without using an injection needle.

Among these, a needleless syringe may be configured to inject an injection component by applying a pressure to an accommodation chamber in which an injection solution is accommodated using a pressurized gas, a spring, or an electromagnetic force. For example, a configuration in which a plurality of nozzle holes are formed inside a syringe main body and a piston that is driven during injection is arranged to correspond to each nozzle hole may be used (Patent Document 1). With such a configuration, an injection solution is sprayed simultaneously from a plurality of nozzle holes and uniform injection into a target is realized. Then, a plasmid containing a luciferase gene can be injected into rats and cells can be transferred with high efficiency.

In addition, there is a form in which a pressurized gas is used as an injection power source for an injection solution in a needleless syringe. For example, a pressurization form in which a high pressure is instantaneously applied in the initial stage of injection, and the applied pressure is then gradually reduced over 40 to 50 msec may be exemplified (Patent Document 2).

However, there are no reports in which a solution containing biomolecules can be directly injected into the cell nucleus of a wide range of injection targets by an injector with high efficiency. In addition, there are no reports focusing on conditions for injecting a solution containing biomolecules from an injector required for directly injecting a solution containing biomolecules into the cell nucleus of a wide range of injection targets with high efficiency.

PRIOR ART DOCUMENTS

Patent Document

[Patent Document 1] Japanese Patent Application Publication No. 2004-358234

[Patent Document 2] U.S. Patent Application Publication No. 2005/0010168

SUMMARY OF THE INVENTION

Problems to be Solved by the Invention

The present invention has been made in view of such circumstances, and an object of the present invention is to provide an injector that can directly inject a solution containing biomolecules into a cell nucleus of a wide range of injection targets with high efficiency.

Means for Solving the Problems

The inventors conducted extensive studies and as a result, found that, when an ignition device including an ignition charge was used, in an injector which accommodates a solution containing biomolecules, by focusing on an injection speed of the solution containing biomolecules within a certain time from an injection start time of the solution containing biomolecules injected from the injector, the following injector can address the above problems, and thus completed the present invention. The present invention is as follows.

[1] An injector that injects a solution containing biomolecules into an injection target from an injector main body without performing injection through a given structure in a state where the given structure is inserted into the injection target, the injector comprising:

- an accommodation unit for accommodating a solution containing biomolecules; and
- a nozzle unit including an injection port through which the solution containing biomolecules flows and is injected into the injection target, the solution being pressurized by combustion of an ignition charge in an ignition device,
- wherein a maximum injection speed of the solution containing biomolecules between an injection start time of the solution containing biomolecules and a time of 0.20 ms is from 75 m/s to 150 m/s and an injection speed of the solution containing biomolecules of from 75 m/s to 150 m/s lasts for 0.11 ms or longer.

[2] A method of injecting a solution containing biomolecules into a cell nucleus of an injection target using the injector according to [1].

[3] A method of expressing a gene in an injection target, the method comprising

- a step of injecting a solution containing a gene-containing DNA into a cell nucleus of an injection target using the injector according to [1].

Effect of the Invention

According to the present invention, it is possible to provide an injector that can directly inject a solution containing biomolecules into a cell nucleus of a wide range of injection targets with high efficiency.

In addition, it is possible to provide a method of directly injecting a solution containing biomolecules into a cell nucleus of a wide range of injection targets using the injector with high efficiency and a method of expressing genes in a wide range of injection targets using the injector with high efficiency.

MODE FOR CARRYING OUT THE INVENTION

Figure 1:
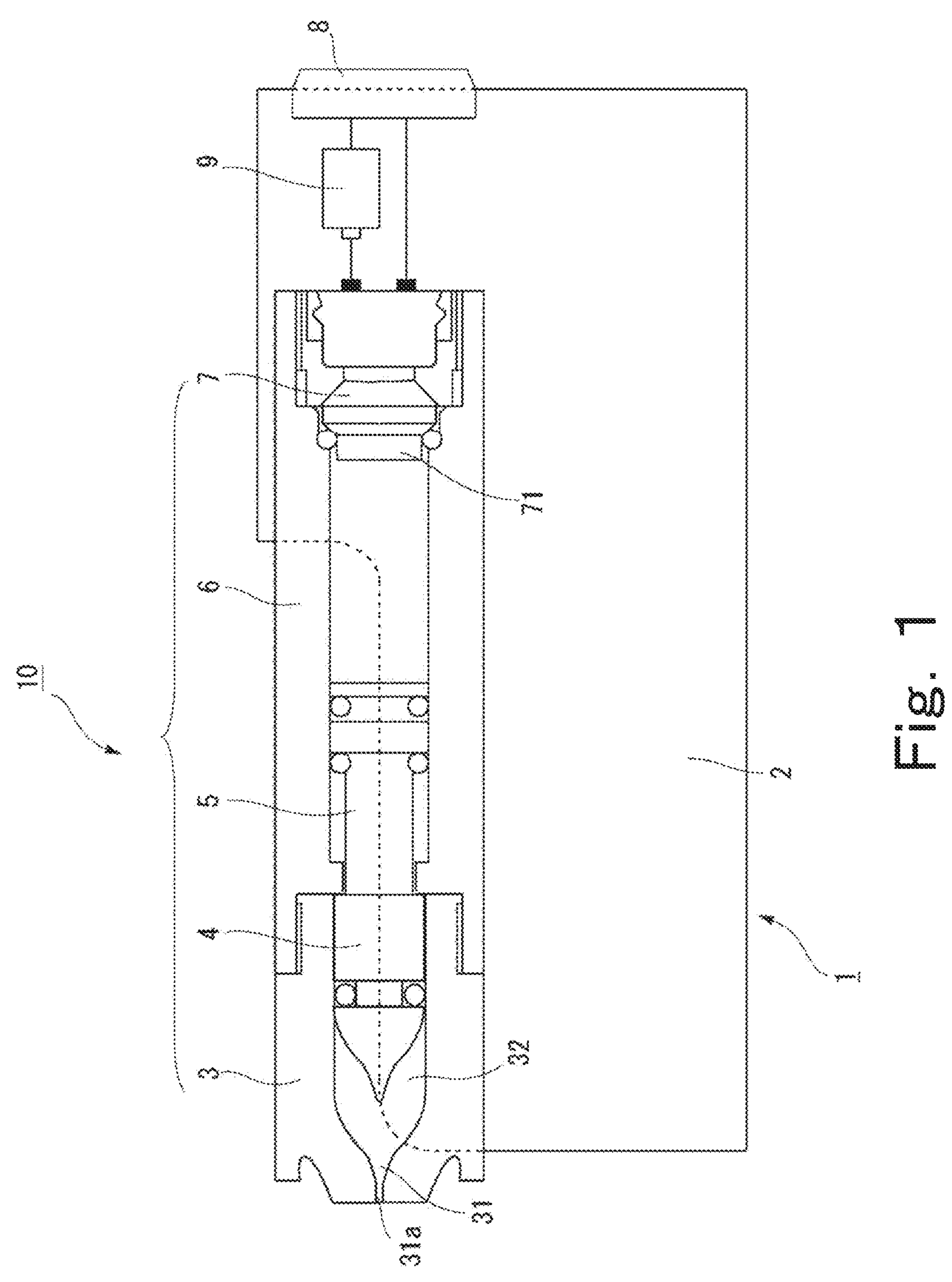
FIG. 1 is a diagram showing a schematic configuration of an injector according to one embodiment of a first aspect of the present invention.

The present invention includes an invention of an injector (first aspect), an invention of a method of injecting a solution containing biomolecules into a cell nucleus of an injection target using the injector (second aspect), and an invention of a method of expressing a gene in an injection target using the injector (third aspect).

<First Aspect>

The first aspect of the present invention is an injector that injects a solution containing biomolecules into an injection target from an injector main body without performing injection through a given structure in a state where the given structure is inserted into the injection target, the injector comprising:

- an accommodation unit for accommodating a solution containing biomolecules; and
- a nozzle unit including an injection port through which the solution containing biomolecules flows and is injected into the injection target, the solution being pressurized by combustion of an ignition charge in an ignition device,
- wherein a maximum injection speed of the solution containing biomolecules between an injection start time of the solution containing biomolecules and a time of 0.20 ms is from 75 m/s to 150 m/s and an injection speed of the solution containing biomolecules of from 75 m/s to 150 m/s lasts for 0.11 ms or longer.

In the injector according to the first aspect of the present invention, combustion energy of the explosive is used as injection energy. In the injector according to the first aspect of the present invention, the maximum injection speed of the solution containing biomolecules between the injection start time of the solution containing biomolecules and a time of 0.20 ms is from 75 m/s to 150 m/s, and the injection speed of the solution containing biomolecules of from 75 m/s to 150 m/s lasts for 0.11 ms or longer, and thus it is possible to directly inject the solution containing biomolecules into a cell nucleus of a wide range of injection targets with high efficiency.

Specifically, for example, when the injection target is cells in a mammalian individual (living body), the maximum injection speed of the solution containing biomolecules between the injection start time of the solution containing biomolecules and a time of 0.20 ms is 75 m/s or more, and thus the solution containing biomolecules penetrates through the epidermis of the mammalian individual (living body), the cells are expected to be deformed due to a shear force when the solution is injected into the dermis, and as a result, the solution containing biomolecules is directly injected into a cell nucleus of cells in the mammalian individual (living body) with high efficiency. The maximum injection speed is preferably 90 m/s or more.

In addition, when the maximum injection speed of the solution containing biomolecules between the injection start time of the solution containing biomolecules and a time of 0.20 ms is 150 m/s or less, the solution is not injected too far in the injection direction (depth direction). For example, when the injection target is a mammalian individual (living body) and the mammal is a female rat (10-week old) or the like, the solution containing biomolecules is expected not to penetrate through the fascia of the rat. The maximum injection speed is preferably 130 m/s or less.

In addition, when the injection speed of the solution containing biomolecules of from 75 m/s to 150 m/s lasts for 0.11 ms or longer, the solution containing biomolecules is expected to spread in the surrounding area not in the injection direction (depth direction), and the solution containing biomolecules is directly injected into a cell nucleus of a wide range of injection targets with high efficiency. For example, when the injection target is cells in a mammalian individual (living body), the solution containing biomolecules that penetrates through the epidermis of the mammalian individual (living body) and is injected into the dermis is expected to spread in the surrounding area not in the injection direction (depth direction), and the solution containing biomolecules is directly injected into a cell nucleus of a wide range of cells in the mammalian individual (living body) with high efficiency.

In the first aspect of the present invention, biomolecules injected into the cell nucleus of the injection target are not particularly limited as long as they function in the cell nucleus or cells of the injection target when they are injected into the cell nucleus of the injection target. In addition, the biomolecules may be a natural product or artificially synthesized product. Examples thereof include nucleic acids or derivatives thereof; nucleosides, nucleotides or derivatives thereof; amino acids, peptides, proteins or derivatives thereof; lipids or derivatives thereof; metal ions; low-molecular-weight compounds or derivatives thereof; antibiotics; and vitamins or derivatives thereof. The nucleic acid may be DNA or RNA, and may include a gene. In examples to be described below, a free Cy3-labeled plasmid DNA is used as biomolecules.

The form of the biomolecules to be injected into the cell nucleus of the injection target and a solvent therefor are not particularly limited as long as biomolecules are stably present and there is no adverse effect such as destruction of the injection target or the cell nucleus of the injection target to be injected, and may be a free form, a form in which biomolecules are fixed to carriers such as nanoparticles, a modified form.

When DNA contains a gene, a design form in which the gene is contained in an expression cassette or expression vector may be exemplified. In addition, for example, the gene may be provided under control of a promoter suitable for the type of the injection target into which the DNA is injected and the injection site. That is, in any of the forms, a known genetic engineering technique can be used.

In the injector according to the first aspect of the present invention, "distal end side" refers to the side on which an injection port through which a solution containing biomolecules is injected from an injector is arranged, and "proximal end side" refers to the side opposite to the distal end side in the injector, and these terms do not limit specific locations or positions.

The injector according to the first aspect of the present invention injects a solution containing biomolecules to the injection target from an injector main body without performing injection through a given structure in the state where the given structure is inserted into the injection target. The injector according to the first aspect of the present invention may have, for example, a given structure such as a catheter for guiding a solution containing biomolecules from an injector main body to an injection target, for example, when a distance from the injector main body to the injection target is large. Therefore, the injector according to the first aspect of the present invention may or may not have such a given structure. However, when the injector has such a given structure, a solution containing biomolecules is not injected into the injection target in the state where the given structure is inserted into the injection target.

In the injector according to the first aspect of the present invention, a driving unit uses combustion energy of an explosive that is ignited by an ignition device as injection energy. That is, the pressurization is pressurization performed by combustion of an ignition charge in the ignition device. Here, when combustion energy of the explosive is used as injection energy, the explosive may be, for example, any explosive among an explosive containing zirconium and potassium perchlorate (ZPP), an explosive containing titanium hydride and potassium perchlorate (THPP), an explosive containing titanium and potassium perchlorate (TiPP), an explosive containing aluminum and potassium perchlorate (APP), an explosive containing aluminum and bismuth oxide (ABO), an explosive containing aluminum and molybdenum oxide (AMO), an explosive containing aluminum and copper oxide (ACO), and an explosive containing aluminum and iron oxide (AFO) or an explosive composed of a plurality of combinations of these. Regarding a feature of these explosives, if the combustion products are gases in a high temperature state, since they do not contain gas components at room temperature, the combustion products after ignition immediately condense.

In addition, when the generated energy of a gas generating agent is used as injection energy, various gas generating agents used in a single base smokeless explosive, a gas generator for an airbag, and a gas generator for a seat belt pretensioner can be used as the gas generating agent.

In the injector according to the first aspect of the present invention, the solution containing biomolecules is not accommodated in a filling chamber from the beginning, and the solution containing biomolecules is accommodated in the filling chamber by sucking through a nozzle having an injection port. In this manner, when a configuration in which a filling operation in the filling chamber is required is used, it is possible to inject any required solution containing biomolecules. Therefore, in the injector according to the first aspect of the present invention, a syringe part is removable.

Hereinafter, regarding an example of an injector according to one embodiment of the first aspect of the present invention, a syringe 1 (needleless syringe) will be described with reference to the drawings. Here, the configuration of the following embodiment is an example, and the first aspect of the present invention is not limited to the configuration of the embodiment. Here, the terms "distal end side" and "proximal end side" are used as terms that represent the relative positional relationships in the syringe 1 in the longitudinal direction. The "distal end side" represents a position near the tip of the syringe 1 to be described below, that is, near an injection port 31*a*, and the "proximal end side" represents a side on the side opposite to the "distal end side" of the syringe 1 in the longitudinal direction, that is, a side on the side of a driving unit 7. In addition, this example is an example in which a DNA solution is used as a solution containing biomolecules, but the first aspect of the present invention is not limited thereto.

(Configuration of Syringe 1)

FIG. 1 is a diagram showing a schematic configuration of the syringe 1 and is a cross-sectional view of the syringe 1 in the longitudinal direction. The syringe 1 has a configuration in which a syringe assembly 10 in which a sub-assembly including a syringe part 3 and a plunger 4 and a sub-assembly including a syringe main body 6, a piston 5, and the driving unit 7 are integrally assembled is mounted in a housing (syringe housing) 2.

As described above, the syringe assembly 10 is configured to be detachable from the housing 2. A filling chamber 32 formed between the syringe part 3 and the plunger 4 included in the syringe assembly 10 is filled with a DNA solution, and the syringe assembly 10 is a unit that is discarded whenever the DNA solution is injected. On the other hand, on the side of the housing 2, a battery 9 that supplies power to an igniter 71 included in the driving unit 7 of the syringe assembly 10 is included. When a user performs an operation of pressing a button 8 provided in the housing 2, supply of power from the battery 9 is performed between an electrode on the side of the housing 2 and an electrode on the side of the driving unit 7 of the syringe assembly 10 via a wiring. Here, the shape and position of both electrodes are designed so that the electrode on the side of the housing 2 and the electrode on the side of the driving unit 7 of the syringe assembly 10 are automatically brought in contact when the syringe assembly 10 is mounted in the housing 2. In addition, the housing 2 is a unit that can be repeatedly used as long as power that can be supplied to the driving unit 7 remains in the battery 9. Here, in the housing 2, when the battery 9 has no power, only the battery 9 may be replaced, and the housing 2 may be continuously used.

In addition, in the syringe main body 6 shown in FIG. 1, no particular additional explosive component is provided, but in order to adjust transition of the pressure applied to the DNA solution via the piston 5, a gas generating agent that generates a gas and the like by combustion of a combustion product generated by explosive combustion in the igniter 71 can be provided in the igniter 71 or in a through-hole of the syringe main body 6. A configuration in which a gas generating agent is provided in the igniter 71 is an already known technique as disclosed in WO 01-031282, Japanese Patent Application Publication No. 2003-25950, and the like. In addition, regarding an example of a gas generating agent, a single base smokeless explosive including 98 mass % of nitrocellulose, 0.8 mass % of diphenylamine, and 1.2 mass % of potassium sulfate may be exemplified. In addition, various gas generating agents used in a gas generator for an airbag and a gas generator for a seat belt pretensioner can be used. When the dimensions, the size, the shape, and particularly, the surface shape of the gas generating agent when provided in the through-hole is adjusted, it is possible to change a combustion completion time of the gas generating agent, and thus the transition of the pressure applied to the DNA solution can be a desired transition, that is, a transition in which the DNA solution can be appropriately injected into the injection target. In the first aspect of the present invention, the driving unit 7 includes a gas generating agent and the like used as necessary.

(Injection Target)

In the first aspect of the present invention, the injection target has no limitation, and may be any of cells, cells in cell sheets, cells in tissues, cells in organs (body organs), cells in organ systems, and cells in individuals (living bodies). Examples of a preferable injection target include injection targets derived from mammals. The injection target is more preferably cells in a mammalian individual (living body), still more preferably cells in the skin, and yet more preferably cells in one or more tissues selected from the group consisting of intradermal, subcutaneous and cutaneous muscles. In this case, a method in which a solution containing biomolecules is injected from an injector into a skin surface of a mammalian individual (living body), and injected from the skin surface into cells in one or more tissues selected from the group consisting of intradermal, subcutaneous and cutaneous muscles in the skin can be used.

In addition, a system in which a solution containing biomolecules is injected from an injector into an injection target may be any of an in vitro system, an in vivo system, and an ex vivo system.

In addition, the mammal is not particularly limited, and examples thereof include humans, mice, rats, guinea pigs, hamsters, cows, goats, sheep, swine, monkeys, dogs, and cats. In addition, depending on the injection target, a form in which humans are excluded from mammals may be exemplified.

(Method of Confirming that Solution Containing Biomolecules is Directly Injected into Cell Nucleus of Wide Range of Injection Targets)

A method of confirming that a solution containing biomolecules is directly injected into a cell nucleus of a wide range of injection targets is not particularly limited, and a known biological technique can be used. For example, a method in which biomolecules are fluorescently labeled in advance, injected into a cell nucleus of an injection target, and then observed under a fluorescence microscope may be exemplified. In examples to be described below, a Cy3-labeled plasmid V7905 (commercially available from Mirus Bio LLC.) is used as DNA that is directly injected into a cell nucleus of cells in the mammalian individual (living body) and DAPI is used as a nuclear staining dye. For example, a sample can be prepared by acquiring a tissue immediately after injecting DNA and separating it into pieces. In this case, DAPI staining may be performed simultaneously. Red fluorescence is exhibited at a position at which the Cy3-labeled plasmid V7905 is injected, and blue fluorescence is exhibited due to DAPI at a position of the cell nucleus. Therefore, according to observation under a fluorescence microscope, a position at which blue purple fluorescence is exhibited can be identified as a position of the Cy3-labeled plasmid V7905 directly injected into the cell nucleus.

<Second Aspect>

The second aspect of the present invention is a method of injecting a solution containing biomolecules to a cell nucleus of an injection target using the injector of the first aspect.

The description of the first aspect of the present invention above applies to the injector, the injection target, and the solution containing biomolecules in the second aspect of the present invention.

<Third Aspect>

The third aspect of the present invention is a method of expressing a gene in an injection target, the method comprising a step of injecting a solution containing a gene-containing DNA into a cell nucleus of an injection target using the injector of the first aspect.

The description of the first aspect of the present invention described above applies to the injector, the injection target, and the solution containing a gene-containing DNA in the third aspect of the present invention.

EXAMPLES

Hereinafter, the present invention will be described in more detail with reference to examples, but the present invention is not limited to the following examples without departing from the spirit and scope of the invention.

(Evaluation of Injection Speed of Injector)

Example 1

The injector shown in FIG. 1 (nozzle diameter: diameter of 0.1 mm) was filled with 100 μL of water, and the injection speed of water from the injection start time of water due to combustion of an ignition charge was evaluated. Regarding the explosive, 35 mg of an explosive containing zirconium and potassium perchlorate (ZPP) was used, and no gas generating agent was used. The injection speed of water was obtained by imaging a distal end of an injector using a high-speed camera (FASTCAM SA-X2 commercially available from PHOTRON LIMITED) and calculating the displacement for injected water and time.

Figure 2:
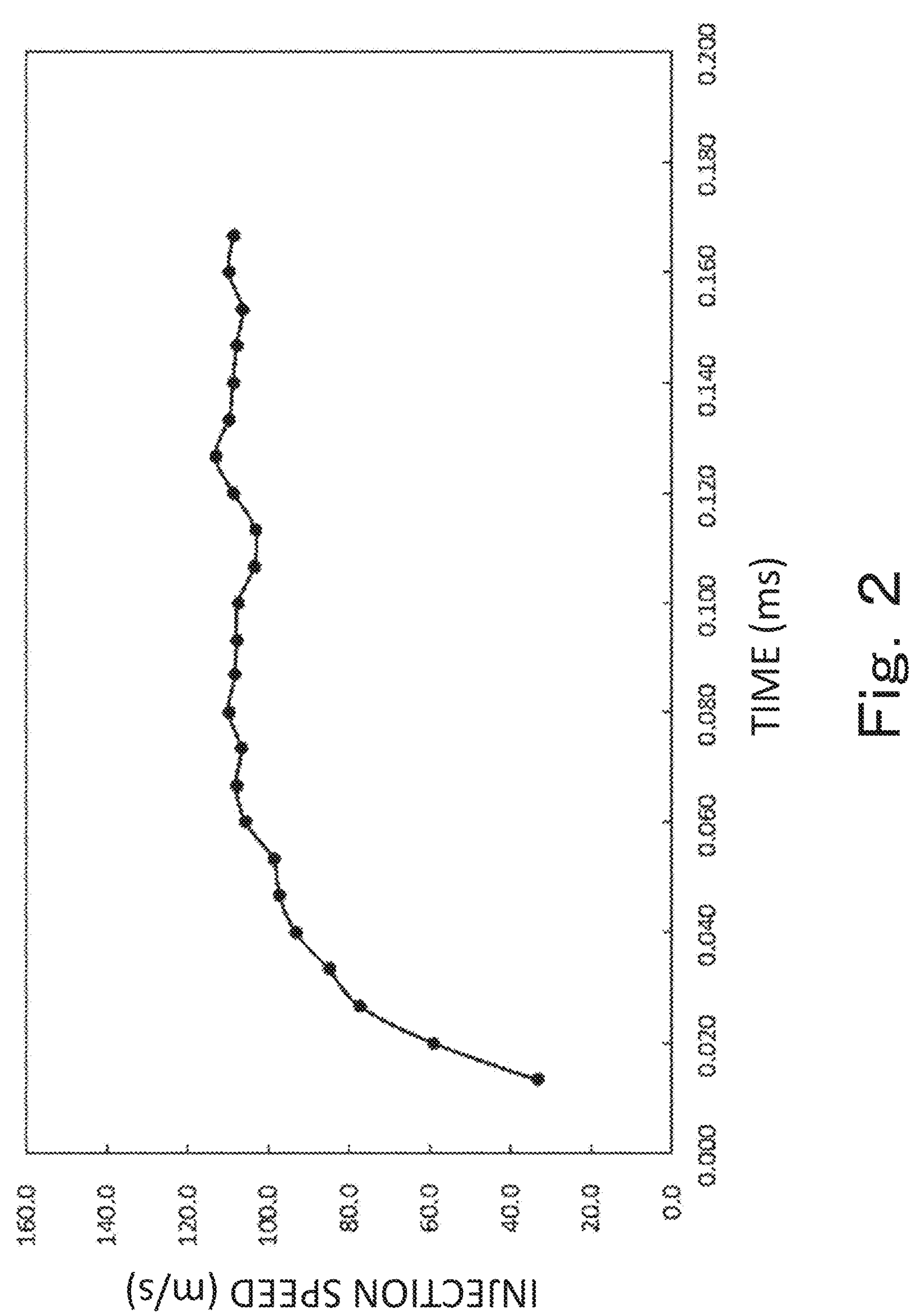
FIG. 2 is a graph showing an injection speed of filled water over time according to one embodiment of the first aspect of the present invention.

FIG. 2 and Table 1 are a graph and a table showing the injection speed of water in Example 1 over time. Here, in Table 1, the injection speed at a certain time was obtained by dividing a difference between the displacement of water at a time one time before the time and the displacement of water at a time one time after the time by the time. For example, the injection speed at a time of 0.013 ms column was obtained by dividing a difference between the displacement of water at a time of 0.000 ms and the displacement of water at a time of 0.020 ms by the time of 0.020 ms.

TABLE 1

| Example 1-1 | |
|---|---|
| Time (ms) | Injection speed (m/s) |
| 0.000 | |
| 0.013 | 33.3 |
| 0.020 | 59.2 |
| 0.027 | 77.3 |
| 0.033 | 85.0 |
| 0.040 | 93.2 |
| 0.047 | 97.2 |
| 0.053 | 98.7 |
| 0.060 | 105.7 |
| 0.067 | 108.0 |
| 0.073 | 106.8 |
| 0.080 | 109.8 |
| 0.087 | 108.3 |
| 0.093 | 108.0 |
| 0.100 | 107.6 |
| 0.107 | 103.5 |
| 0.113 | 103.2 |
| 0.120 | 108.7 |
| 0.127 | 113.1 |
| 0.133 | 109.8 |
| 0.140 | 108.7 |
| 0.147 | 108.0 |
| 0.153 | 106.5 |
| 0.160 | 109.8 |
| 0.167 | 108.7 |

(Test of Injecting DNA Solution into Cell Nucleus of Cells in Mammalian Individual (Living Body))

Example 2

The injector used in Example 1 was filled with 30 μL of a solution containing a Cy3-labeled plasmid V7905 (solvent: endotoxin-free TE buffer, final concentration: 0.1 mg/mL). Regarding the explosive, 35 mg of an explosive containing zirconium and potassium perchlorate (ZPP) was used, and regarding the gas generating agent, 40 mg of a single base smokeless explosive. The solution was injected into the skin of the lumbar back of a female SD rat (10-week old). Here, as described above, no gas generating agent was used in Example 1, but the gas generating agent was used in this example. This is because it is considered that use of a gas generating agent does not affect the initial injection speed defined in the present invention.

Figure 3:
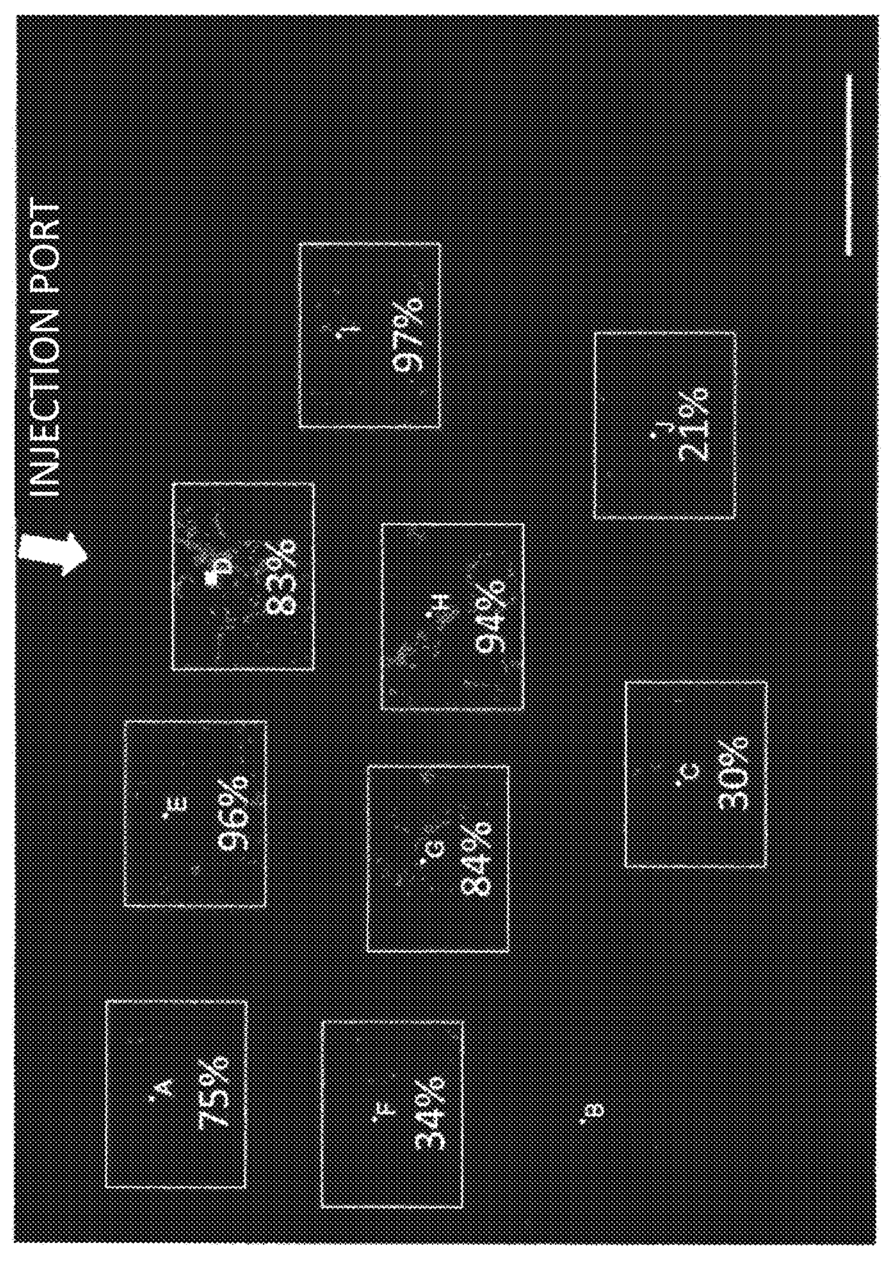
FIG. 3 is a diagram (photograph annotated with drawing) showing a distribution of DNA introduced into a cell nucleus in a mammalian individual (living body) and a mammalian individual (living body) according to one embodiment of a second aspect of the present invention.

Immediately after injection, the skin was removed and frozen in an OCT compound (embedding agent for preparing a frozen tissue section (Tissue Tech O.C.T. Compound), commercially available from Sakura Finetek Japan Co., Ltd.) with dry ice. Using a cryostat (commercially available from Leica), the cross section of the injection part was cut into slices with a thickness of 6 μm and encapsulated with an encapsulant containing DAPI. The fluorescence of the prepared sample was observed under an all-in-one fluorescence microscope (Z-X700, commercially available from Keyence Corporation), and a red fluorescence image of Cy3 and a blue fluorescence image of DAPI were obtained with a thickness of 0.1 to 0.4 μm. In order to obtain an injection distribution in the injection area, images in a plurality of fields were obtained. The results are shown in FIG. 3. The scale bar indicates 0.73 mm.

A proportion of the number of cells into which DNA was directly injected was calculated as follows using a hybrid cell count function. That is, for cells in each analysis target area (each area surrounded by a white frame in FIG. 3), cells in which an area of the purple fluorescence in which the blue fluorescence and the red fluorescence overlapped was 50% or more with respect to the area of cells were defined as cells into which DNA was directly injected, and the number of cells was counted (this is referred to as a number of cells A). On the other hand, a total number of cells in each analysis target area was counted using the number of cell nuclei as an index (this is referred to as a number of cells B). A ratio shown in each analysis target area in FIG. 3 is a ratio of the number of cells A to the number of cells B. Here, the epidermis and hair follicles in which hardly any of the red fluorescence of Cy3 was observed were excluded from the analysis target.

In FIG. 3, in Example 2, a high proportion of DNA was directly injected into a cell nucleus of a wide range of cells around the injection port not in a narrow range immediately below the injection port.

(Evaluation of Gene Expression Using Rats)

Example 3

The injector used in Example 1 was filled with 30 μL of a solution (solvent: endotoxin-free TE buffer, final concentration: 1.0 mg/mL) containing a plasmid pGL3-control vector containing a luciferase gene (commercially available from Promega Corporation), and the solution was injected into the skin of the lumbar back of a female SD rat (10-week old).

Here, as described above, no gas generating agent was used in Example 1, but the gas generating agent was used in this example. This is because it is considered that use of the gas generating agent does not affect the initial injection speed defined in the present invention.

After injection, the rat was returned to a breeding environment and euthanized 24 hours later, and a tissue from the intradermal to skin muscles (that is, intradermal, subcutaneous and cutaneous muscles) was then excised in a circular shape with a diameter of 1 mmϕ around the injection port, and this was used as a "center sample". In addition, a tissue from the intradermal to skin muscles (that is, intradermal, subcutaneous and cutaneous muscles) was excised in a circular shape with a diameter of 1 mmϕ centered at a position about 1.5 to 2 mm away from the injection port, and this was used as an "outer sample". The outer sample was collected at two positions that were point symmetrical around the injection port.

0.1 mL of "Cell Culture Lysis×5" of Luciferase assay system (commercially available from Promega Corporation) diluted fivefold was put into a 2 mL micro tube to prepare a dissolution liquid, and the center sample was added to the dissolution liquid. Next, the micro tube was left in a dry ice atmosphere for about 15 minutes and frozen. It was confirmed that the tube had frozen and it was left to thaw at room temperature for about 20 minutes. This freezing and thawing were repeated three times in total to promote cell destruction. Then, the sample was left for 5 minutes to obtain a supernatant.

In addition, procedures were performed for two outer samples.

The luciferase assay was performed using Lumitester C100 (commercially available from Kikkoman Biochemifa Company). First, the Luciferase Assay Substrate of the Luciferase assay system was returned to room temperature and opened and 10 mL of the Luciferase Assay Buffer returned to room temperature was added thereto. The mixture was lightly shaken to avoid foaming and the dissolved state was confirmed. 100 μL of the mixture was added to a Lumitube and 20 μL of a supernatant sample to be measured was added and pipetting was performed several times so that the mixture became uniform. The sample was put into a Lumitester measurement chamber within about 20 seconds and measured to obtain a luminous intensity. In the outer sample, the average value of luminous intensities of two outer samples was used as the luminous intensity of the outer sample. The luminous intensity (RLU) correlated with the expression level of the luciferase gene. Here, analysis was performed by excluding those determined as being insufficient for obtaining the outer sample due to a narrow injection range of the DNA solution in the rat.

Figure 4:
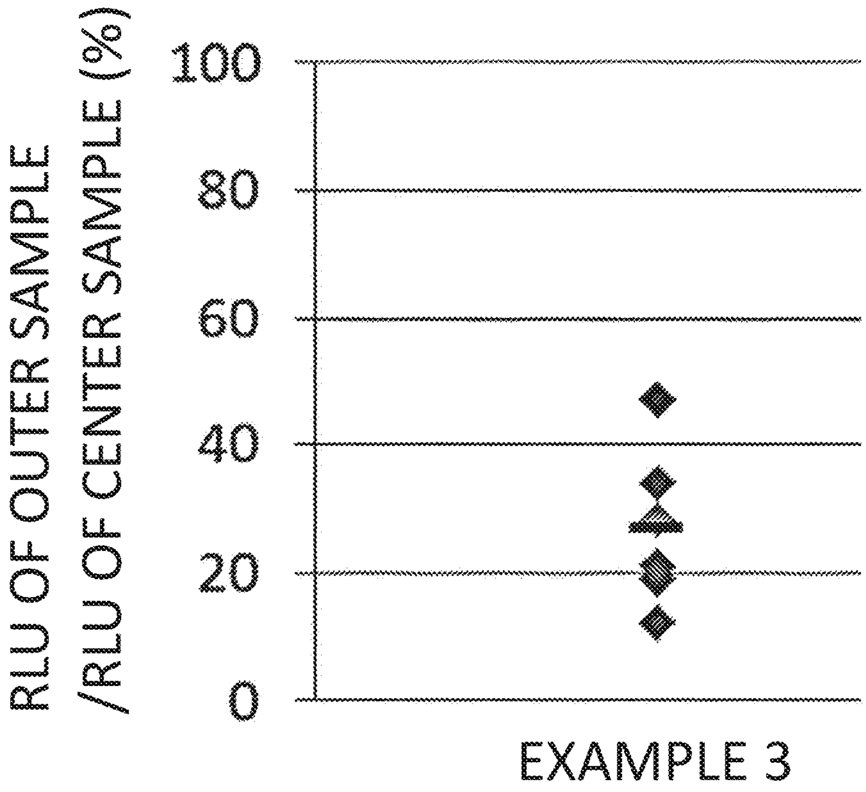
FIG. 4 is a graph showing numerical values expressed in percentage and obtained by dividing a luminous intensity (RLU) of an outer sample by a luminous intensity (RLU) of a center sample after a plasmid DNA solution containing a luciferase gene is administered to rats according to one embodiment of a third aspect of the present invention.

FIG. 4 shows the results of numerical values expressed in percentage and obtained by dividing the RLU of the outer sample by the RLU of the center sample for the luminous intensity (RLU) obtained in Example 3. In FIG. 4, the rhombus plot indicates each numerical value, and the horizontal bar indicates the average value.

In FIG. 4, in Example 3, in the outer sample, a relatively high gene expression was observed, and efficient gene expression was obtained not only in a narrow range centered on the injection port but also in a wide range of tissues centered on the injection port.

DESCRIPTION OF REFERENCE NUMERALS

1: Syringe, 2: Housing, 3: Syringe part, 4: Plunger, 5: Piston, 6: Syringe main body, 7: Driving unit, 8: Button, 9: Battery, 10: Syringe assembly, 31: Nozzle unit, 31*a*: Injection port, 32: Filling chamber, 71: Igniter

The invention claimed is:

1. An injector that injects a solution containing biomolecules into an injection target from an injector main body without performing injection through a given structure in a state where the given structure is inserted into the injection target, the injector comprising:

an accommodation unit accommodating a solution containing biomolecules;

an ignition device configured to combust an ignition charge;

a piston;

a driving unit comprising a gas generating agent configured to generate a gas based on a combusted ignition charge; and a nozzle unit including an injection port through which the solution containing biomolecules flows, wherein the driving unit controls the piston and a combustion process of the ignition device to:

start an injection of the solution containing biomolecules at an injection start time of 0 ms, vary an injection speed of the solution containing biomolecules during a time period of 0 ms and 0.20 ms, and maintain a maximum injection speed of the solution containing biomolecules in a range of 75 m/s to 150 m/s during the time period for 0.11 ms or longer.

2. A method of injecting a solution containing biomolecules into a cell nucleus of an injection target using the injector according to claim 1.

3. A method of expressing a gene in an injection target, the method comprising:

injecting a solution containing a gene-containing DNA into a cell nucleus of an injection target using the injector according to claim 1.

4. The injector of claim 1, wherein the driving unit is configured to control the piston, the ignition device, and the nozzle unit to adjust the transition of the pressure applied to the solution containing biomolecules via the piston and further cause that the solution containing biomolecules penetrates through an epidermis of a living body, cells are deformed due to a shear force when the solution containing biomolecules is injected into a dermis, and the solution containing biomolecules is directly injected into a cell nucleus of cells in the living body.

5. The injector of claim 1, wherein the driving unit is configured to change a combustion completion time of the gas generating agent, and change the transition of the pressure applied to the solution containing biomolecule to a desired transition based on adjusting at least one of a dimension, a size, or a shape of the gas generating agent.

* * * * *